United States Patent [19]

Rantala

[11] Patent Number: 5,957,838
[45] Date of Patent: Sep. 28, 1999

[54] PATIENT MONITORING SYSTEM

[75] Inventor: Börje Rantala, Helsinki, Finland

[73] Assignee: Instrumentarium Oy, Helsinki, Finland

[21] Appl. No.: 08/886,351

[22] Filed: Jul. 1, 1997

[30] Foreign Application Priority Data

Jul. 2, 1996 [FI] Finland ................................. 962727

[51] Int. Cl.$^6$ ..................................................... A61B 5/00
[52] U.S. Cl. ........................................... 600/300; 600/301
[58] Field of Search ..................................... 359/144, 152, 359/163; 600/300, 301

[56] References Cited

U.S. PATENT DOCUMENTS

| | | | |
|---|---|---|---|
| 4,688,579 | 8/1987 | Inahara . | |
| 4,715,385 | 12/1987 | Cudahy et al. . | |
| 5,126,937 | 6/1992 | Yamaguchi et al. | 600/301 |
| 5,412,497 | 5/1995 | Kaetsu et al. | 359/163 |
| 5,479,288 | 12/1995 | Ishizuka et al. | 359/152 |
| 5,535,031 | 7/1996 | Cecchini | 359/152 |
| 5,781,321 | 7/1998 | Kobayashi | 359/152 |

FOREIGN PATENT DOCUMENTS

| | | |
|---|---|---|
| 519 137 | 12/1992 | European Pat. Off. . |
| 755 653 | 1/1997 | European Pat. Off. . |
| 89 98 906 | 2/1990 | Germany . |
| 87/05120 | 8/1987 | WIPO . |

OTHER PUBLICATIONS

A Body Surface Mapping Unit for Recording During Coronary Angioplasty, R. S. McLeod et al, Proceedings of the Annual International Conference of the IEEE EMBS, vol. 10, No. 1/4, Nov. 4–7, 1988, New Orleans, pp. 97–98.

*Primary Examiner*—Robert L. Nasser
*Attorney, Agent, or Firm*—Andrus, Sceales, Starke & Sawall

[57] ABSTRACT

Patient monitoring system for the monitoring of a patient's condition using monitoring parameters determined about the patient, said system comprising a central data processing unit (1), peripherals (2, 3, 4); parameter modules (5), each comprising a preamplifier (6) for preliminary amplification of a parameter signal, an A/D converter (7) for converting the parameter signal into digital form, and a first optic transmitter-receiver (8) for isolating the data transfer of the digital parameter signal; data transfer equipment for data communication between the first transmitter-receivers (8) of the parameter modules and the central data processing unit (1); a coupling frame (9), on which parameter modules (5) can be detachably mounted: parameter sensors (10) to be connected to the patient and a sensor cable (11) for each parameter sensor to pass the parameter signal from the parameter sensor to the preamplifier corresponding to the parameter concerned. The coupling frame (9) is made of a material substantially optically permeable to light to allow it to function as a medium for optic data communication. The data transfer equipment for communication between a first transmitter-receiver (8) and the central data processing unit (1) comprises a second optic transmitter-receiver (12) attached to the coupling frame (9) to achieve data communication together with the first transmitter-receivers using optic signals travelling inside the material of the coupling frame (9).

37 Claims, 3 Drawing Sheets

PATIENT MONITORING SYSTEM

BACKGROUND OF THE INVENTION

The present invention relates to a patient monitoring system.

In prior art, there are patient monitoring systems for monitoring a patient's condition using monitoring parameters defined for the patient. Typical monitoring parameters include parameters descriptive of respiration, temperatures, EKG, invasive and noninvasive blood pressure, oxygen saturation of haemoglobin and similar quantities.

Patient monitoring systems are used e.g. in connection with anaesthetic treatment in operating theatres, in recovery rooms and in intensive monitoring. Previously known systems include a system commercially available under the trademark Datex AS/3™ (manufactured by Instrumentarium Oy, Finland). A diagram representing this prior-art system is presented in FIGS. 1 and 2 as far as necessary for an understanding of the present invention. The system comprises a central data processing unit 1 controlling all functions of the system. Connected to it are a number of peripherals, such as a display unit 3, by means of which parameters measured from the patient can be continuously monitored in the form of curves and numeric values. Moreover, the system comprises a keyboard 2, a printer 4 and other peripherals. The system is of a modular design, comprising a number of different parameter modules 5, which can be selected for inclusion in the system assembly according to the monitoring need. Individual parameter modules are designed to measure one or more monitoring parameters.

As can be seen from FIG. 2, each parameter module comprises a preamplifier 6 for preliminary amplification of a parameter signal and an A/D converter 7 for converting the parameter signal into digital form. Each parameter module may comprise, as in the Datex AS/3™ system, a data processing unit 13, such as a microprocessor or the like, for the processing of a digital parameter signal and execution of tasks associated with measurement parameters, e.g. supervision of the operation of a module etc. The data processing unit may also control e.g. pneumatic components and work up the measurement results for input to the central data processing unit 1. At the same time, the central data processing unit 1 is performing higher-level tasks, such as collecting trends, taking care of various alarms and the set-up and control of a user interface. Furthermore, the system comprises a first optical transmitter-receiver 8 for isolating the data transfer of the digital parameter signal to achieve patient isolation. In this prior-art module, an optical data transfer and power supply isolation interface, achieved using a transformer, is placed on a circuit board. Further, as can be seen from FIG. 1, this prior-art system comprises data transfer equipment to allow data communication between the central data processing unit 1 and the optical first transmitter-receivers 8 of the parameter modules 5. The parameter modules are mounted on a common coupling frame 9, in which they can be locked, detached and replaced.

The system further comprises parameter sensors 10 to be connected to the patient and sensor cables 11 for each parameter sensor to pass the parameter signal from the parameter sensor to the pre-amplifier 6 of the parameter module corresponding to the parameter concerned.

For instance, in the prior-art Datex AS/3™ system (FIG. 1), the coupling frame 9 is a box with one side open, into which the parameter modules 5 can be inserted side by side. The back side of the module and correspondingly the coupling frame back wall, against which the back side is placed when the module is mounted, are provided with electric connectors for data transfer 28 and power supply 29, aligned with each other so that when the module is inserted into the coupling frame, the connectors 28, 29 of the module plug into corresponding connectors in the coupling frame back wall, thus connecting the data transfer central unit of the module to a data communication bus 30, 31 (module bus 30, AS/3 bus 31) and the power supply line to a voltage source 32.

A problem with the type of connection described above is that the connectors of the module and coupling frame have to be accurately located at the right positions relative to each other with very small tolerances to ensure successful simultaneous engagement of several adjacent connectors. A further problem is the large number of plug-in connectors. The connectors tend to gather impurities and are difficult to clean, which becomes a problem in an environment supposed to be sterile. Another problem in this prior-art system is that the cables from the modules to the patient must be relatively long because the prior-art coupling frame box cannot be placed near the patient. Further problems result from the long cables as adjacent cables run in a disorderly manner, hitching together into a cable mess. On the other hand, optic connectors are very expensive.

BRIEF SUMMARY OF THE INVENTION

The object of the present invention is to eliminate the drawbacks referred to above.

A specific object of the invention is to produce a system which employs a minimum number of electric and optic connectors and in which the coupling frame can be placed beside the patient.

A further object of the invention is to produce a system in which the coupling frame can be easily cleaned and even sterilized.

The system of the invention is characterized by what is presented in the claims.

According to the invention, the coupling frame is made of a material optically substantially permeable to light to allow it to function as a medium of optic data communication. The data transfer equipment for data communication between a first transmitter-receiver and a central unit comprises a second optic transmitter-receiver connected to the coupling frame to achieve data communication together with the first transmitter-receivers using optic signals travelling inside the material of the coupling frame.

The invention has the advantage that the coupling frame, in addition to serving as a means of mechanical attachment, also takes care of the functions of a data transfer channel, making it possible to achieve a cheap structure and to substantially reduce the number of optic and/or electric connectors, thus also avoiding the problems relating to the precision of placement of connectors required for mechanical connection. The coupling frame also provides an interface for the isolation of data transfer. The coupling frame together with parameter modules attached to it can be placed right beside the patient, and the data transfer will not be disturbed even if the coupling frame should be splashed with patient excretions, blood, etc., because the communication is effected using optic signals travelling inside the coupling frame material. Further, as the modules and the coupling frame can be placed near the patient, short sensor cables from the modules to the patient can be used, which means less cable mess. The second optic transmitter-receiver can be placed in any suitable place on the coupling frame and it is able to pick up the data transfer signals from inside the coupling frame material.

In an embodiment of the system, the parameter module comprises a data processing unit, such as a microprocessor, for the processing of a digital parameter signal to allow duplex data communication and for the execution of tasks related to a measurement parameter, such as supervision of the operation of a module and the like.

In an embodiment of the system, the coupling frame is made of translucent, light-scattering plastic, such as milk-coloured plastic, e.g. nylon. The essential point is that the material is pervious to light. In translucent plastic, which is not transparent, the optic signal is evenly scattered in the entire coupling frame material, from which it can be picked up by a transmitter-receiver. Alternatively, the coupling frame nay be made of transparent plastic, such as polycarbonate or polymethyl-methacrylate. In this case, the signal advances via surface reflections. If the coupling frame is made of clear plastic, its surface can be coated with a specular substance, e,g. silver-plated, to enhance reflections, leaving an opening in the coating in the area opposite to the first transmitter-receiver of the module.

In an embodiment of the system, the transmitter-receivers are designed to use a wavelength range between 600–1500 nm. Preferably the transmitter-receivers are consistent with the standard "Serial Infrared Physical Layer Link specification by IrDA" (Infrared Data Association, P.O. Box 3843, Walnut Creek, Calif. 94598). The above-mentioned standard prescribes norms for data transfer components intended for the PC environment.

In an embodiment of the system, the central data processing unit controls the data communication on a time sharing principle between the first transmitter-receivers and the second transmitter-receiver. The data communication may be half-duplex between the first transmitter-receivers and the second transmitter-receiver. Alternatively, the data communication may be full-duplex between the first transmitter-receivers and the second transmitter-receiver. In full-duplex communication, the transmitter of the first transmitter-receiver and the receiver of the second transmitter-receiver work on a different wavelength than the receiver of the first transmitter-receiver and the transmitter of the second transmitter-receiver.

In an embodiment of the system, the coupling frame is provided with power cables for the supply of electric current to the parameter modules.

In an embodiment of the system, the parameter module comprises a frame box, in which the electronics of the parameter module is mounted. The coupling frame (or frame box) is provided with a mounting groove. The frame box (or coupling frame) is provided with a mounting rail fitted to be slid into the mounting groove.

In an embodiment of the system, the mounting groove and mounting rail are provided with power connectors designed to connect galvanically to each other when the mounting rail is slid into the mounting groove. The sliding mounting can easily be so implemented that when a module is mounted in the coupling frame, any dirt is removed from the groove and the connector contact surfaces at the same time.

In an embodiment of the system, the mounting groove and mounting rail together form a so-called dove-tail or hammer-head joint. The power connectors are disposed near the bottom of the mounting groove so as to be inaccessible to touch.

In an embodiment of the system, the supply of power to the parameter modules is effected using a high-frequency alternating current safe against treatment injury, suitably a 20–2000 kHz alternating current, preferably a 100 kHz alternating current. When a high-frequency alternating current is used, damaged cables are not dangerous to the patient even if a damaged cable should come into contact with the patient. Each parameter module comprises an isolation transformer to achieve so-called patient isolation of power supply. Patient isolation is regulated by patient isolation standards (IEC 601-1, UL 544 specifications) By placing the isolation transformer in the parameter module, the power supply isolation interface is advantageously implemented in combination with the data transfer isolation.

In an embodiment of the system, the data transfer equipment for the transmission of a digital parameter signal from the parameter modules to the central data processing unit comprises a master cable containing a signal conductor for data communication and a power conductor for the supply of electric current to the power connectors, said signal and power conductors forming a single integral cable. As there is only one master cable leading from the coupling frame near the patient to the central data processing unit and the cable may be thin and flexible, a substantial reduction of cable mess is achieved.

In an embodiment of the system, the master cable comprises a first end, which is connected to the coupling frame, and a second end, which is connected to the central data processing unit. Supply of electric current to the power conductor and data transfer to the signal conductor is isolated again at the second end of the master cable. Without detriment to patient isolation, the master cable may be freely placed anywhere near the patient or on the floor, where it can be wheeled over with carts etc. without the risk of an electric shock.

In an embodiment of the system, the coupling frame is a plate-like body of a shape substantially resembling a rectangular prism, the mounting groove being formed in the broad side of said body. The frame box of the parameter module is a substantially flat body having the shape of a rectangular prism, with a mounting rail on its broad side and a connector for the connection of a sensor cable on its end face. The parameter module frame boxes have a symmetric structure with respect to the mounting rail and groove so that adjacent parameter modules can be mounted on the coupling frame in either orientation as desired so that the connectors on adjacent parameter modules are directed in opposite directions relative to each other.

BRIEF DESCRIPTION OF THE SEVERAL VIEWS OF THE DRAWING

In the following, the invention is described in detail by the aid of embodiment examples by referring to the attached drawing, in which FIG. 1 in a diagram representing a prior-art system.

DETAILED DESCRIPTION OF THE INVENTION

Figure 1:
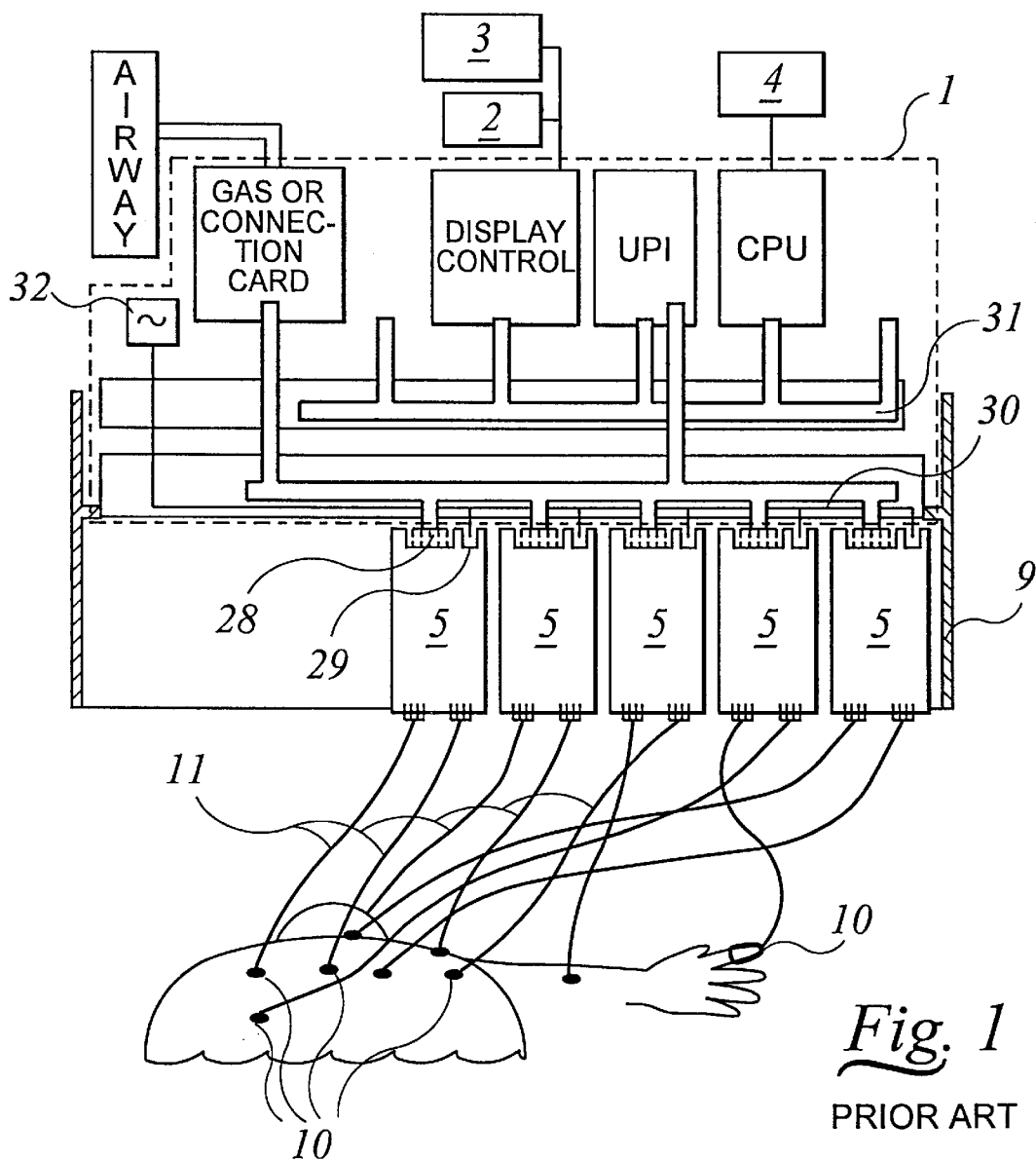
Figure 2:
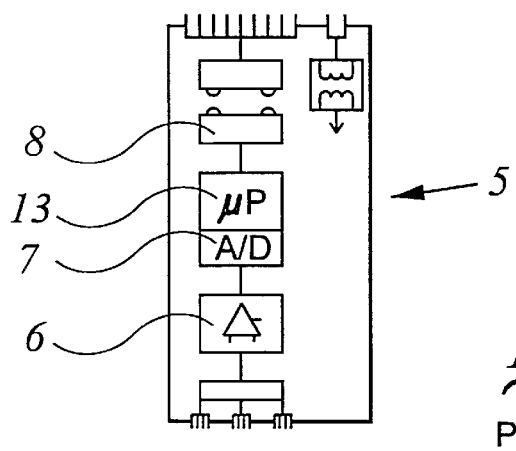
FIG. 2 is a diagram representing a module of the prior-art system in FIG. 1.

FIGS. 1 and 2 represent a prior-art system as described in the general part of the application.

Figure 3:
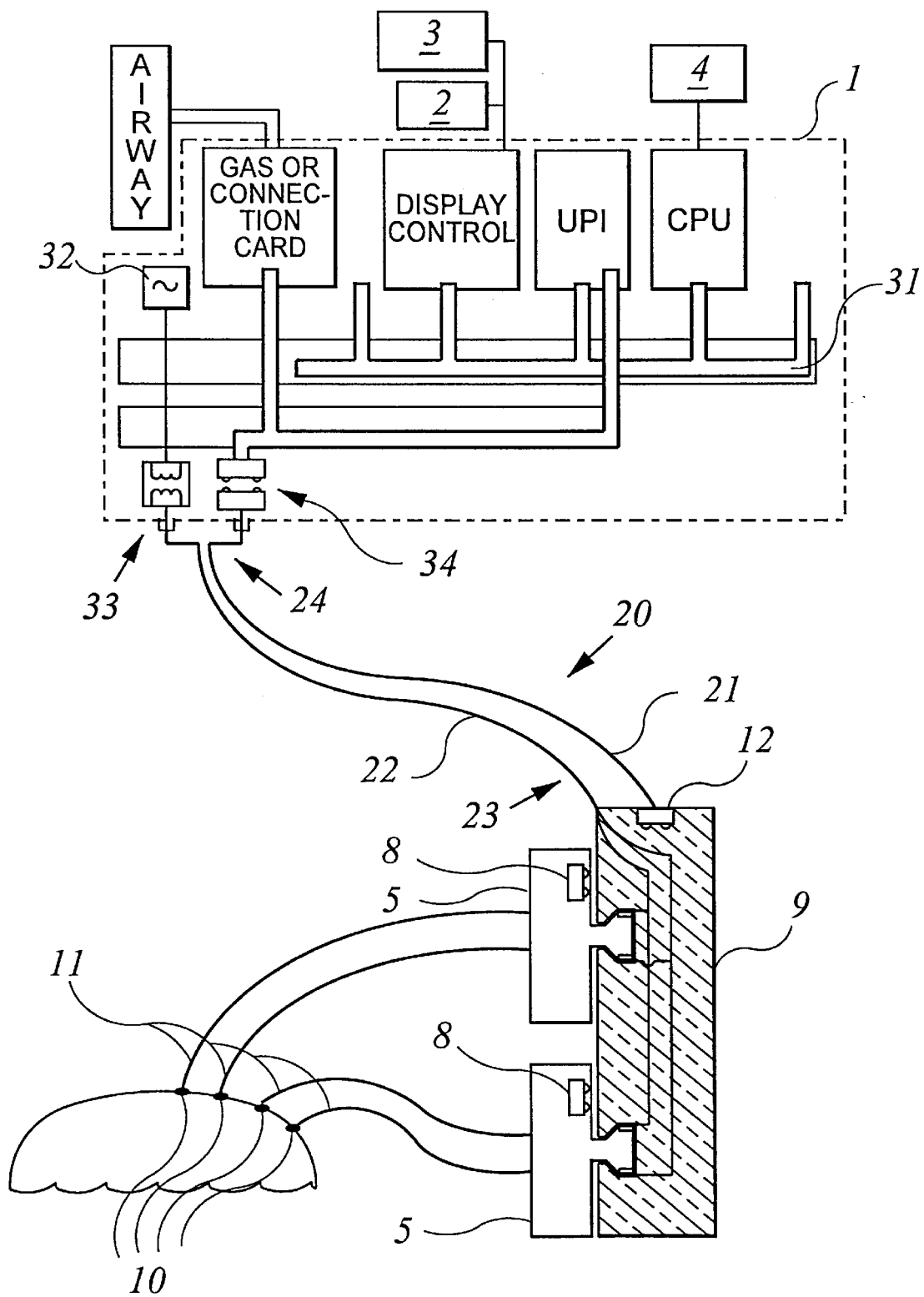
FIG. 3 is a diagram representing an embodiment of the system of the invention.

FIG. 3 shows a patient monitoring system by means of which the condition of a patient can be monitored by using monitoring parameters determined for the patient.

The system comprises a central data processing unit 1, encircled in the figure with a broken line. The system also comprises a number of peripherals, such as a display unit 3, a keyboard 2, a printer 4 etc, which are connected to the central data processing unit. These will not be described here in detail. The system is of a modular design, comprising a number of parameter modules 5, which can be selected for inclusion in the assembly according to the monitoring need in each case. Individual parameter modules perform one or more monitoring functions. Obviously the structural details of the modules 5 and the components used in them depend on the parameter to be monitored and may vary considerably. The structural details of the modules are not described here because such matters are part of the know-how of a person skilled in the art.

A feature common to all modules is that each of them comprises a preamplifier 6 for preliminary amplification of the parameter signal, an A/D converter 7 for converting the parameter signal into digital form, and a first optic transmitter-receiver 8 for isolating the data transfer of the digital parameter signal. Moreover, the parameter module 5 may comprise a data processing unit 13, such as a microprocessor, for the processing of the digital parameter signal so as to allow duplex data communication and for the execution of tasks associated with the measurement parameter, e.g. supervision of the operation of the module and similar tasks.

The monitoring parameters are measured by means of parameter sensors 10 connected to the patient's body, each sensor being provided with a sensor cable 11 to pass the parameter signal from the parameter sensor to the preamplifier 6 of the parameter module corresponding to the parameter concerned. The parameter modules 5 are detachably mounted together on a coupling frame 9 to form a unitary assembly.

Figure 4:
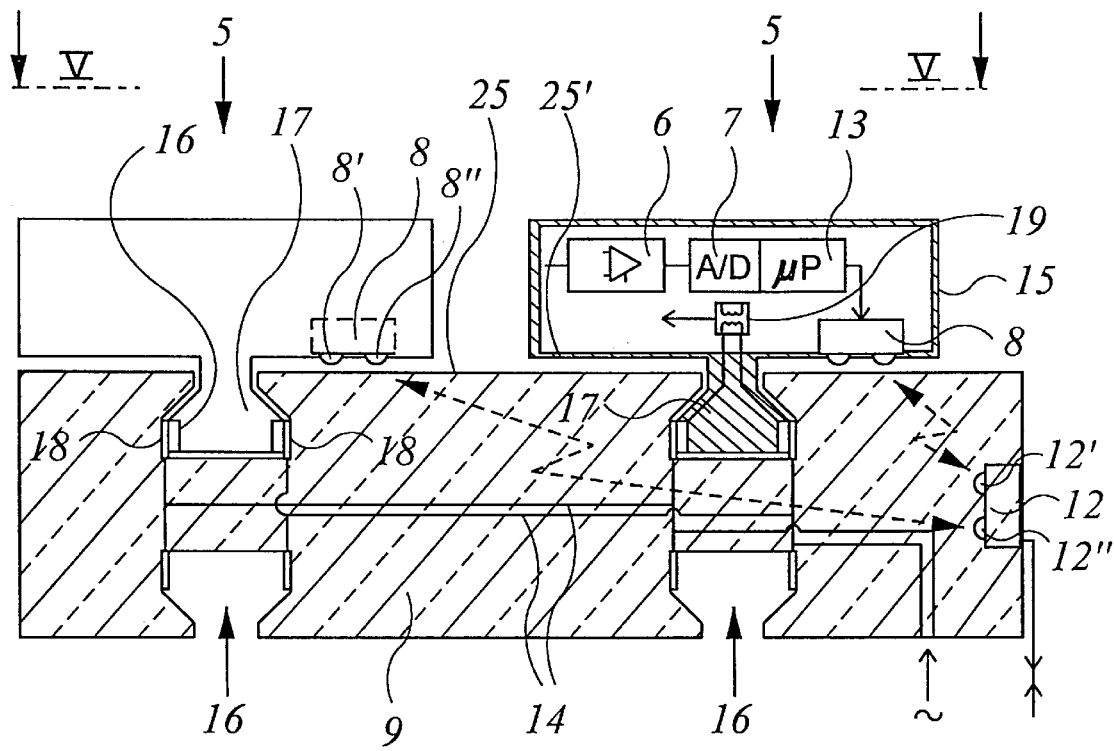
FIG. 4 is a diagram representing a magnified cross-section of the coupling frame in the system in FIG. 3 and of the modules mounted in it.

As shown in FIGS. 3 and 4, the coupling frame 9 is made of a material optically pervious to light to allow it to function as are medium of optical data communication. To achieve data communication between the first transmitter-receiver B and the central data processing unit 1, a second transmitter-receiver 12 connected to the coupling frame 9 is provided to effect data communication together with the first transmitter-receivers using optic signals travelling inside the coupling frame material. The coupling frame 9 may be made of light-scattering, translucent plastic, such as milk-coloured plastic, e.g. nylon. Polycarbonate with a translucent colouring is another alternative. The coupling frame 9 may also be made of transparent plastic, such as polycarbonate or polymethyl-acrylate.

To make it possible to use commercially available standard components for the data transfer, the transmitter-receivers 8, 12 are consistent with the "Serial Infrared Physical Layer Link specification by IrDA" (Infrared Data Association, P.O. Box 3843, Walnut Creek, Calif. 94598) standard, which defines the properties of components intended for the PC environment. Therefore, the transmitter-receivers 8, 12 use a wavelength range between 600–1500 mm for data transfer.

The first transmitter-receivers 8 of the modules communicate on a time-sharing principle with the second transmitter-receiver 12 in the coupling frame 9. For the sake of simplicity, the data communication is effected in half-duplex node between the first transmitter-receivers 6 and the second transmitter-receiver 12, in other words only one transmitter is active at any given instant of time, so that no signal collisions occur in the optic bus formed inside the coupling frame 9 material.

By using several light wavelengths, the data communication can also be effected in full-duplex mode between the first transmitter-receivers 8 and the second transmitter-receiver 12. In this case, the transmitter 8' of the first transmitter-receiver 8 and the receiver 12" of the second transmitter-receiver 12 are arranged to work on a different wavelength than the receiver 8' of the first transmitter-receiver 8 and the transmitter 12' of the second transmitter-receiver 12. The differentiation can be effected using light filters placed over the optic components.

As shown in FIG. 4, the coupling frame 9 is provided with power conductors 14 for the supply of operating voltage to the parameter modules 5. The parameter module 5 comprises a frame box 15, inside which the above-described electronics of the parameter module 5 is assembled. The coupling frame 9 is provided with a mounting groove 16. The frame box 15 comprises a mounting rail 17 structurally integrated with the box and fitted to be slid into the mounting groove 16. The mounting groove 16 and mounting rail 17 together form a mechanical dove-tail or hammer-head joint which keeps the modules in position on the coupling frame 9 and allows them to be easily detached from it. The mounting groove 16 and mounting rail 17 are provided with power connectors 18 placed near the bottom of the mounting groove 16 so as to be inaccessible to touch. The power connectors are galvanically connected to each other when the mounting rail 17 is inserted into the mounting groove 16. At the same time, any dirt that may have gathered on the slide rail is removed from it.

The operating power to the parameter modules 5 is supplied via the power conductors 14 and power connectors 18 with a high-frequency, preferably 100 kHz alternating current, which is reliable in respect of patient safety. Thus, possible damage to the conductors involves no risk of electric shock. Each parameter module 5 contains an isolation transformer 19 to achieve patient isolation of the power supply. Therefore, the module need not be provided with oscillator or other circuits like those required in prior-art modules. The structure of the isolation transformers and optic transmitter-receivers is obvious to the person skilled in the art, so they need not be described here in detail.

As shown in FIG. 3, the data transfer equipment for the transmission of the digital parameter signal from the parameter modules 5 to the central data processing unit 1 comprises a master cable 20, which contains a signal conductor 21 for data communication and a power conductor 22 for the supply of electric current to the power connectors 18. The signal and power conductors form a single unitary cable assembly. The master cable 20 comprises a first end 23, which is connected to the coupling frame 9, and a second end 24, which is connected to the central data processing unit 1. At the second end 24 of the master cable 20, the supply of electric current to the power conductor 22 is isolated by means of an isolating transformer 33, while data transfer to the signal cable 21 is isolated by means of an optic transmitter-receiver combination. In this way, a floating master cable 20 is achieved, in other words, patient isolation consistent with standard requirements (IRC 601-1, UL 544) is achieved between the master cable and the rest or the electronics in the central data processing unit. Therefore, the master cable 20 may be of a thin construction and it can be freely placed neat the patient or on the floor as it is isolated at both ends.

Figure 5:
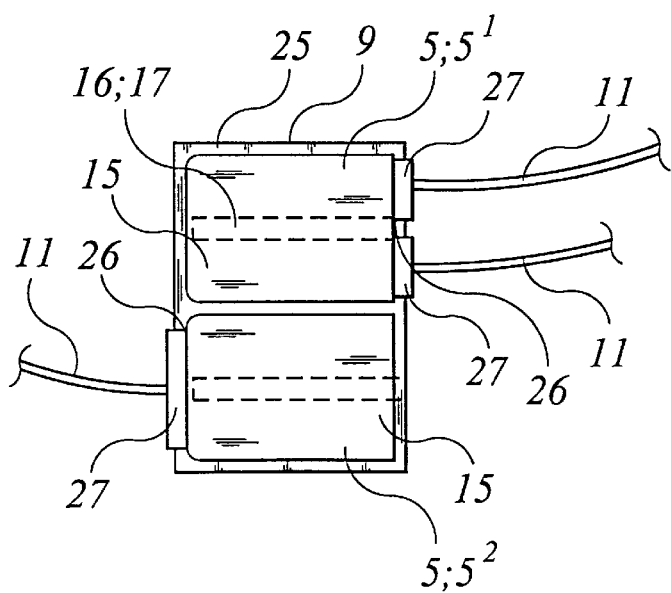
FIG. 5 presents the coupling frame and modules of FIG. 4 as seen from the direction V—V, and rotated 90°.

FIGS. 4 and 5 show that the coupling frame 9 is a plate-like body having the shape of a rectangular 30 prism, the mounting groove 16 being formed in its broad side 25. The frame box 15 of the parameter module 5 is a substantially flat body having the shape of a rectangular prism, with a mounting rail 17 on its broad side 25'. The end face 26 of the frame box is provided with a connector 27 for the connection of the sensor cable 11. The frame boxes 15 of the parameter modules 5 are of a symmetric construction with respect to the mounting rail 17 and groove 16 so that adjacent parameter modules can be mounted on the coupling frame 9 in either orientation as desired so that the connectors 27 of adjacent parameter modules are directed in S opposite directions relative to each other. This further reduces the cable mess. Let us suppose for instance that we nave a coupling frame 9 placed near a patient and, mounted on it, an EKG module $5^1$ with the sensors placed on the patient's breast and the cables 11 running in a corresponding direction, and a module $5^2$ for measuring invasive blood pressure with a sensor attached to the patient's hand. In this situation the modules are advantageously so mounted that the sensor cables from the modules $5^1$, $5^2$ run in opposite directions substantially towards the object of measurement, thus further reducing the cable length and cable mess.

The invention is not restricted to the examples of its embodiments described above, but many variations are possible within the framework of the inventive idea defined by the claims.

I claim:

1. Patient monitoring system for the monitoring of a patient's condition using monitoring parameters determined for the patient, said system comprising a central data processing unit (1), a plurality of parameter modules (5), each parameter module being adapted to measure one or more monitoring parameters, each of said modules comprising an A/D converter (7) for converting a parameter signal obtained from a parameter sensor into a digital parameter signal, and a first optic transmitter-receiver (8) for isolating data transfer of the digital parameter signal, a coupling frame (9), on which said parameter modules (5) can be detachably mounted, the coupling frame (9) being made of a material substantially optically permeable to light to allow it to function as a medium of optic data communication for the first optic transmitter-receivers; and data transfer equipment for coupling the first transmitter-receivers (8) of the parameter modules to the central data processing unit (1) for establishing data communication therebetween, the data transfer equipment for communication between a first transmitter-receivers (8) and the central data processing unit (1) including a second optic transmitter-receiver (12) attached to the coupling frame (9) to achieve data communication with the first transmitter-receivers using optic signals travelling inside the material of the coupling frame (9) between the first and second transmitter-receivers.

2. System as defined in claim 1, wherein at least one of the parameter modules (5) further comprises a preamplifier (6) for preliminary amplification of the parameter signal and a data processing unit (13) for the processing of the digital parameter signal to allow duplex data communication and for the execution of tasks associated with the measurement parameter.

3. System as defined in claim 1 wherein the coupling frame (9) is made of translucent, light-scattering plastic.

4. System as defined in claim 3 wherein the coupling frame (9) is made from milk-colored plastic.

5. System as defined in claim 3 wherein the coupling frame (9) is made from nylon.

6. System as defined in claim 1, wherein the coupling frame (9) is made of transparent plastic.

7. System as defined in claim 4 wherein the coupling frame (9) is made from one of polycarbonate or polymethylmethacrylate.

8. System as defined in claim 1, wherein the transmitter-receivers (8, 12) are designed to use a wavelength range between 600–1500 nm.

9. System as defined in claim 1, wherein the transmitter-receivers are consistent with the standard "Serial Infrared Physical Layer Link specification by IrDA".

10. System as defined in claim 1, wherein the central data processing unit controls the data communication on a time sharing principle between the first transmitter-receivers (9) and the second transmitter-receiver (12).

11. System as defined in claim 10, wherein the data communication is half-duplex between the first transmitter-receivers (8) and the second transmitter-receiver (12).

12. System as defined in claim 10, wherein the data conmunication is full-duplex between the first transmitter-receivers (8) and the second transmitter-receiver (12).

13. System as defined in claim 12, wherein the transmitter (8') of the first transmitter-receiver (8) and the receiver (12") of the second transmitter-receiver (12) work at a different wavelength than the receiver (8") of said given first transmitter-receiver (8) and the transmitter (12') of the second transmitter-receiver (12).

14. System as defined in any one of claims 1, wherein the coupling frame (9) is provided with power conductors (14) for the supply of electric current to the parameter modules (5).

15. System as defined in claim 11, wherein the power conductors are suitable for supplying high-frequency alternating current power in a range of 20–2000 kHz to the parameter modules.

16. System as defined in claim 15, wherein the power conductors are suitable for supplying 100 kHz alternating current power to the parameter modules.

17. System as defined in claim 15, wherein said parameter module includes an isolating transformer (19) for providing patient isolation in the supply of electric current to the parameter modules (5).

18. System as defined in claim 14, wherein the data transfer equipment for the transmission of a digital parameter signal from the parameter modules (5) to the central data processing unit (1) comprises at least one signal conductor (21) for data communication and at least one power conductor (22) for the supply of power to the power connectors (14), said signal and power conductors forming portions of a single integral cable 20.

19. System as defined in claim 18, wherein the cable (20) comprises a first end (23), which is connected to the coupling frames (9), and a second end (24), which is coupled to the central data processing unit; and wherein said second end includes means for isolating the supply of power to the power conductors (14) and means for isolating the data transfer in the signal conductor (21).

20. System as defined in claim 1, wherein each parameter module (5) comprises a frame box (15) containing circuitry of the parameter module; one of the coupling frame (9) and frame box (15) is provided with a mounting groove (16); and the other of the frame box (15) and coupling frame (9) is provided with a mounting rail (17) fitted to be slid into the mounting groove (16).

21. System as defined in claim 20, wherein the mounting grooves (16) and mounting rails (17) are provided with power connectors (18) designed to connect galvanically to each other when the mounting rail is slid into a mounting groove.

22. System as defined in claim 21, wherein a mounting groove (16) and mounting rail (17) together form a dove-tail or hammer-head joint; and the power connectors (18) are disposed near the bottom of the mounting groove (16) so as to be inaccessible to touch.

23. System as defined in claim 20, wherein a mounting groove (16) and mounting rail (17) together form a dove-tail or hammer-head joint.

24. System as defined in claim 12 wherein, the coupling frame (9) is substantially a plate-like body of a shape resembling a rectangular prism having major and minor side surfaces, a plurality of adjacent mounting grooves (16) being formed in a major side surface (25) of said plate-like body; and the frame box (15) of each of each of the parameter modules (5) is a substantially flat body having the shape of a rectangular prism having major and minor side surfaces and end surfaces, a mounting rail (17) being placed on a major side surface (25) of said flat body of each of said parameter modules.

25. System as defined in claim 20, wherein a connector (27) for the connection of a sensor cable (11) is located on an end surface of said flat body of each of said parameter modules, and wherein the frame boxes of said parameter modules have a symmetric structure relative to the mounting rails and grooves so that the parameter modules can be mounted on the coupling frame to position the connectors in opposite directions relative to each other.

26. System as defined in claim 1 wherein the system comprises peripherals (2, 3, 4), including a display unit, a keyboard, and a printer, which are connected to the central data processing unit (1).

27. Apparatus providing patient condition parameter data for use by a patient monitoring system, the parameter data defining conditions of the patient, said apparatus comprising:

a plurality of parameter modules (5) adapted to measure one or more monitoring parameters, said module comprising a frame box containing an A/D converter (7) for converting a parameter signal obtained from a parameter sensor into a digital parameter signal, and containing a first optic transmitter-receiver (8) for isolating data transfer of the digital parameter signal, and a coupling frame (9), on which said parameter modules (5) can be detachably mounted, the coupling frame (9) being made of a material substantially optically permeable to light to allow it to function as a medium of optic data communication for the first optic transmitter-receivers, said coupling frame having a second optic transmitter-receiver (12) attached thereto to achieve data communication with the first transmitter-receiver using optic signals travelling inside the material of the coupling frame (9) between the first and second transmitter-receivers, said second transmitter-receiver providing the patient condition parameter data for use by the patient monitoring system;

one of said coupling frame and frame box being provided with a mounting groove, the other of said frame box and coupling frame being provided with a mounting rail fitted to be slid into the mounting groove.

28. Apparatus as defined in claim 27 wherein the mounting grooves and mounting rails are provided with power connectors which are electrically connected to each other when a mounting rail is slid into a mounting groove.

29. Apparatus as defined in claim 28 wherein a mounting groove and mounting rail together form a dove-tail or hammer-head joint and wherein the power connectors are disposed near the bottom of the mounting groove so as to be inaccessible to touch.

30. Apparatus as defined in claim 27 wherein a mounting groove and mounting rail together form a dove-tail or hammer-head joint.

31. Apparatus as defined in claim 27 wherein the coupling frame is substantially a plate-like body of a shape resembling a rectangular prism having major and minor side surfaces, a plurality of adjacent mounting grooves being formed in a major side surface of said plate-like body and the frame box of each of said parameter modules is a substantially flat body having the shape of a rectangular prism having major and minor side surfaces and end surfaces, a mounting rail being placed on a major side surface of said flat body of each of said parameter modules.

32. Apparatus as defined in claim 31 wherein a connector for the connection of a sensor cable is located on an end surface of said flat body of each of said parameter modules and wherein said frame boxes of said parameter modules have a symmetric structure relative to the mounting rails and grooves so that the parameter modules can be mounted on the coupling frame to position the connectors in opposite directions relative to each other.

33. Apparatus as defined in claim 27 wherein the coupling frame is made of a translucent, light scattering plastic.

34. Apparatus as defined in claim 27 wherein the coupling frame is made of a transparent plastic.

35. A coupling frame for use with a plurality of parameter modules (5) monitoring a patient's condition using monitoring parameters determined for the patient, said module having an A/D converter (7) for converting a parameter signal obtained from a parameter sensor into a digital parameter signal, and a first optic transmitter-receiver (8) for isolating data transfer of the digital parameter signal, each of said parameter modules having a mounting rail, said coupling frame having a plurality of mounting grooves for receiving the mounting rails of said parameter modules so that said parameter modules (5) can be detachably mounted on said mounting frame, the coupling frame (9) being made of a material substantially optically permeable to light to allow it to function as a medium of optic data communication for the first optic transmitter-receivers, said coupling frame having a second optic transmitter-receiver (12) to achieve data communication with the first transmitter-receiver using optic signals travelling inside the material of the coupling frame (9) between the first and second transmitter-receivers, said mounting grooves and mounting rails together forming a dove-tail or hammer-head joint, said coupling frame having power conductors for the supply of power to said parameter modules, said power conductors being disposed near the bottom of said mounting grooves so as to be inaccessible to touch.

36. The coupling frame as defined in claim 35 wherein the coupling frame is made of a translucent, light scattering plastic.

37. The coupling frame as defined in claim 35 wherein the coupling frame is made of transparent plastic.

* * * * *

UNITED STATES PATENT AND TRADEMARK OFFICE
CERTIFICATE OF CORRECTION

PATENT NO. : 5,957,838
DATED : September 28, 1999
INVENTOR(S) : Rantala

It is certified that error appears in the above-indentified patent and that said Letters Patent is hereby corrected as shown below:

In the claims:

Claim 9, col. 8, line 14, delete "are" and substitute therefor ---provide data communication---; Claim 10, col. 9, line 18, delete "(9)" and substitute therefor ---(8)---; Claim 13, col. 8, line 27, delete "the" and substitute therefor ---a given; Claim 21, col. 9, line 4, delete "the" and substitute therefor ---a---

Signed and Sealed this

Tenth Day of April, 2001

Attest:

NICHOLAS P. GODICI

*Attesting Officer*     *Acting Director of the United States Patent and Trademark Office*